(12) United States Patent
Bellafiore et al.

(10) Patent No.: US 7,704,262 B2
(45) Date of Patent: Apr. 27, 2010

(54) HOLLOW SUTURE NEEDLE WITH HANDLE

(75) Inventors: Mark A. Bellafiore, Clearwater, FL (US); Steven E. Fitts, Largo, FL (US); Peter C. Miller, Largo, FL (US)

(73) Assignee: Linvatec Corporation, Largo, FL (US)

( * ) Notice: Subject to any disclaimer, the term of this patent is extended or adjusted under 35 U.S.C. 154(b) by 1304 days.

(21) Appl. No.: 10/872,246

(22) Filed: Jun. 18, 2004

(65) Prior Publication Data

US 2005/0283171 A1 Dec. 22, 2005

(51) Int. Cl.
*A61B 17/04* (2006.01)
(52) U.S. Cl. .................................... 606/144
(58) Field of Classification Search ......... 606/144–148, 606/139, 153–157; 279/77, 78, 81, 89, 93, 279/94, 91, 97
See application file for complete search history.

(56) References Cited

U.S. PATENT DOCUMENTS

| 3,663,028 | A | * | 5/1972 | King et al. ...................... 279/91 |
| 4,890,615 | A | * | 1/1990 | Caspari et al. ............... 606/146 |
| 5,336,229 | A | * | 8/1994 | Noda ........................... 606/144 |
| 5,520,702 | A | * | 5/1996 | Sauer et al. .................. 606/144 |
| 5,582,615 | A | * | 12/1996 | Foshee et al. ................ 606/139 |
| 5,643,292 | A | * | 7/1997 | Hart ............................ 606/144 |
| 5,908,428 | A | * | 6/1999 | Scirica et al. ................ 606/139 |
| 5,997,552 | A | * | 12/1999 | Person et al. ................ 606/139 |
| 6,585,744 | B1 | * | 7/2003 | Griffith ........................ 606/144 |
| 2005/0165417 | A1 | * | 7/2005 | Sauer et al. .................. 606/144 |

* cited by examiner

*Primary Examiner*—Todd E Manahan
*Assistant Examiner*—Lindsey Bachman
(74) *Attorney, Agent, or Firm*—Gene Warzecha

(57) ABSTRACT

A suture needle instrument having improved connection means enabling a hollow suture needled to be attached to a handle in a variety of orientations. The suture needle is provided with user accessible suture channels and suture advancing wheels to facilitate cleaning and repair.

3 Claims, 7 Drawing Sheets

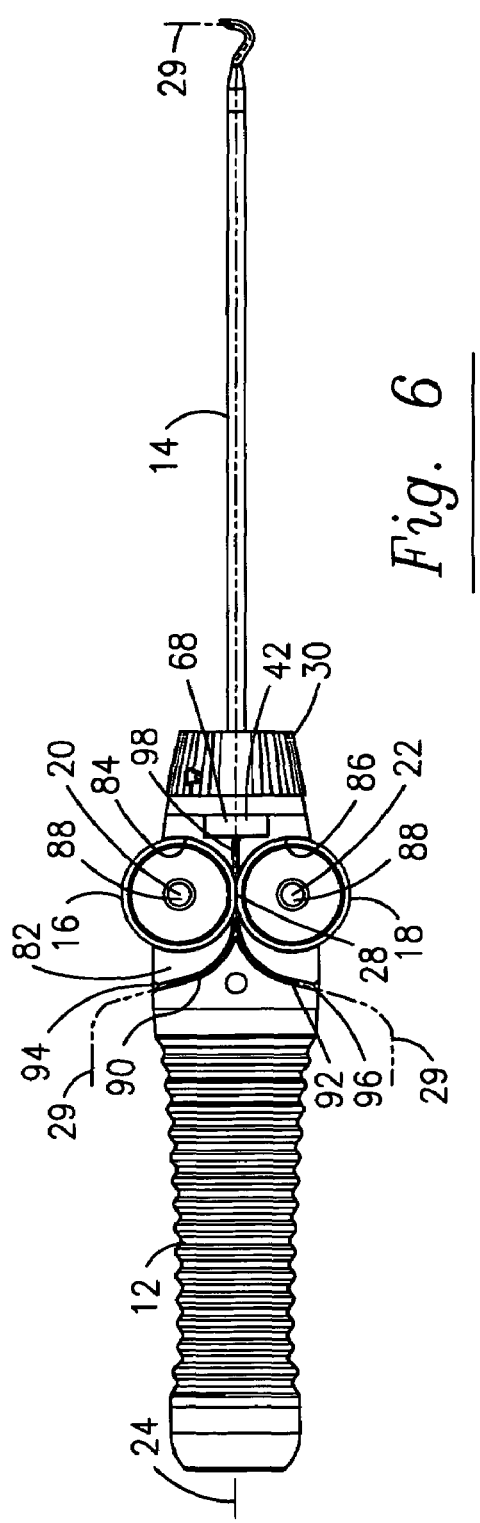
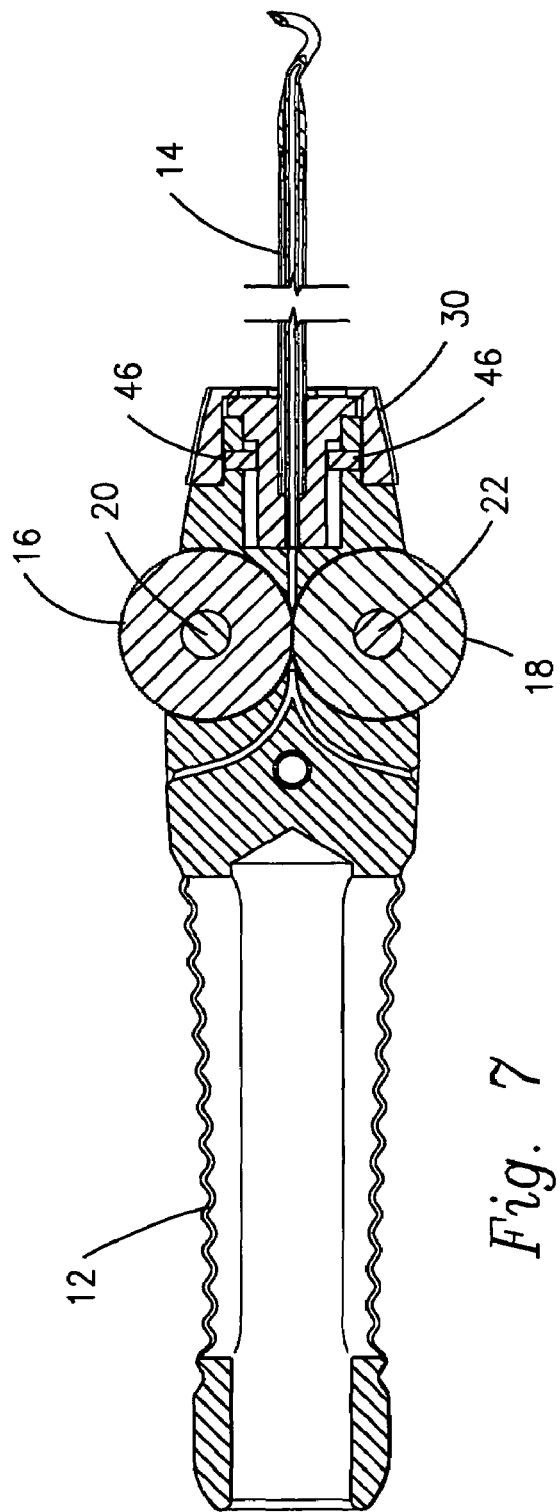

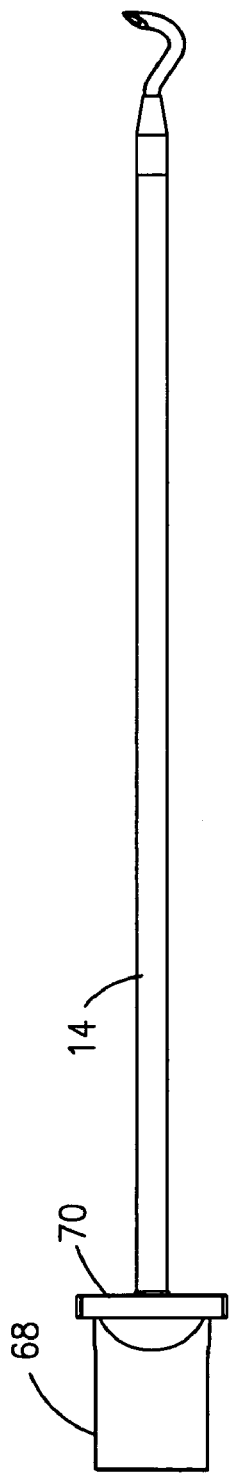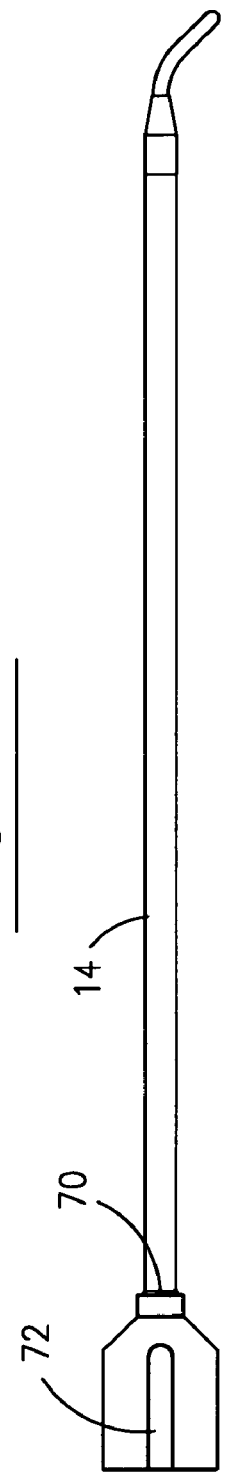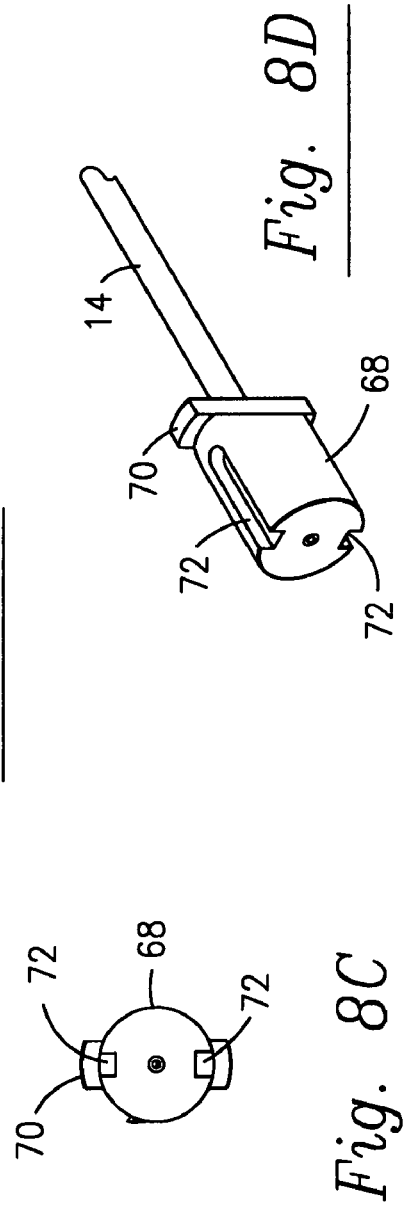
Fig. 8A
Fig. 8B
Fig. 8C
Fig. 8D

HOLLOW SUTURE NEEDLE WITH HANDLE

BACKGROUND OF THE INVENTION

1. Field of the Invention

The invention relates to devices used for suturing tissue during surgical procedures. More particularly, the invention relates to devices used to advance suture through tissue via a hollow needle piercing the tissue to be sutured. Still more particularly, the invention relates to suturing devices for use during endoscopic surgical procedures.

2. Background of the Prior Art

Devices for facilitating the suturing of tissue during endoscopic surgical procedures are commonly used. One such device is the Spectrum® tissue repair system made by Linvatec Corporation. The system incorporates a suture hook handle adapted to receive a variety of suture hooks, i.e. hollow needles, each suture hook having a distal tip shaped in varying ways. The suture hook handle is provided with a pair of opposed suture advancing wheels, the perimeters of which are covered with an elastomeric material. The wheels are aligned in a common plane and rotatable about their respective axes which are spaced a predetermined distance apart so that the perimeters of the wheels may be adjacent or contiguous to each other. The suture hook handle comprises a pair of diametrically opposed suture passageways leading to the nip of the wheels so that a suture inserted into a selected passageway is guided to the nip of the wheels and by rotation of one of the wheels may be advanced through the lumen of the selected needle.

The various suture hooks are attachable to the suture hook handle by means of an axially aligned recess at the distal end of the handle, the recess being adapted to receive a complementarily shaped hub attached to the proximal end of each suture hook. The end wall of the recess has an axially aligned aperture to receive suture from the nip of the wheels and guide it to the needle lumen. Once a suture hook is assembled with the suture hook handle, it is secured thereto by a transverse set screw which is advanced radially into the recess to engage a dimple on the hub of the suture hook to secure the hook to the handle.

While offering significant advantages and facilitating the suturing of tissue during endoscopic surgical procedures, the prior art device is not easily disassembled for cleaning or repair and does not allow reorientation of the suture hook during a surgical procedure. Orientation of this prior art device is generally accomplished by inserting a different suture hook rather than simply reorienting the one currently in use. Accordingly, it is an object of this invention to produce a suture hook system overcoming the disadvantages of the prior art device.

It is also an object of this invention to produce a suture hook handle which is easily disassembled for cleaning or repair.

It is also an object of this invention to produce a suture hook system which enables the reorientation of a selected suture hook during a surgical procedure.

SUMMARY OF THE INVENTION

These and other objects of the invention are achieved by the embodiments of the invention disclosed herein. In one aspect, the invention comprises a suture passer comprising a handle having an axis and a path within the handle for guiding suture to a predetermined point. A hollow needle is attachable to the handle and a user-operable wheel means is mounted on the handle for engaging the suture at the predetermined point and moving it into the lumen of the hollow needle. The hollow needle has a proximal hub which cooperates with a collet on the distal end of the handle to produce a connector means interposed between the handle and the needle for attaching them together in a selected one of a plurality of predetermined rotational positions. The connector means comprises an extension member at the distal end of the handle, the extension having a recess and a collar axially aligned with and rotatably attached to the extension member. The collar has a proximal end and a distal end and is rotatable between an open position, in which it can receive the hollow needle, and a closed position in which it can hold the hollow needle to the handle. A hub is fixedly attached to the proximal end of the hollow needle, the hub comprising a body adapted to be received in the recess and an axial bore within the body. The bore is aligned with the lumen of the hollow needle and the predetermined point when the needle is assembled with the handle. A locking means is adapted to be engaged by the collar when it is in the closed position.

In another aspect, the aforementioned handle comprises a sagittal planar surface within the handle. A pair of wheels is attached to the handle, each rotatable about its own axis, with the axes of the wheels parallel to each other, perpendicular to the sagittal plane and spaced apart a predetermined distance to enable the perimeters of the wheels to be adjacent to each other at a first point. At least one first suture passageway is provided for guiding a suture from an aperture on the surface of the handle to the predetermined point between the wheels. The first suture passageway comprises a groove in the sagittal planar surface, the groove extending between the aperture on the surface of the handle and a second point adjacent and proximal to the first point.

BRIEF DESCRIPTION OF THE DRAWINGS

FIG. 6 is a side elevational view of the suture hook system shown in FIG. 1 with a cover portion removed from the handle.

FIG. 7 is a cross-sectional view of FIG. 2 taken along the lines 7-7.

FIG. 8*a* is a side elevational view of a suture hook for use with the suture hook handle shown in FIG. 1.

FIG. 8*b* is a top plan view of FIG. 8*a*.

FIG. 8*c* is a left end view of FIG. 8*a*.

FIG. 8*d* is a left side perspective view of FIG. 8*a*.

BRIEF DESCRIPTION OF THE PREFERRED EMBODIMENT

Figure 1:
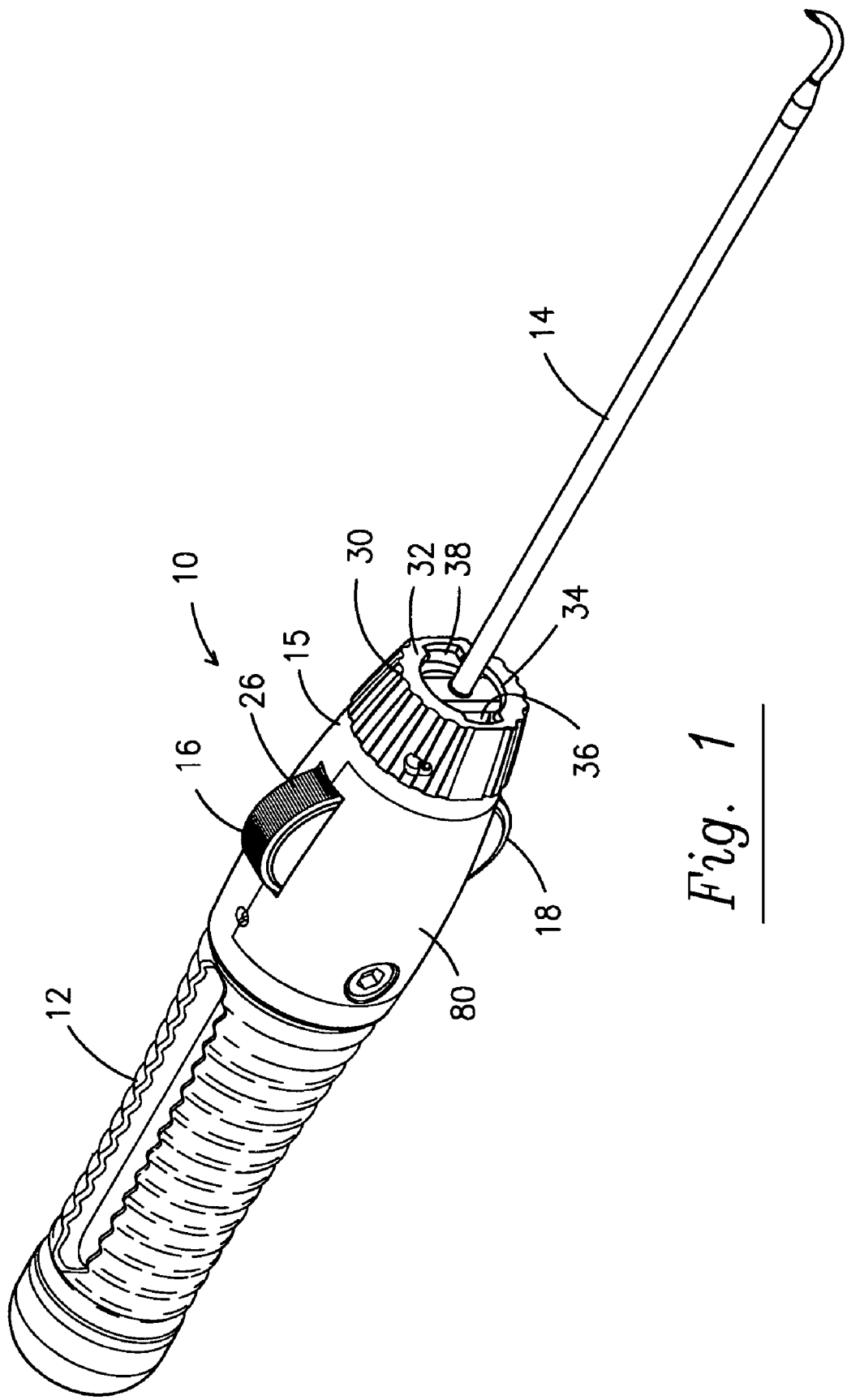
FIG. 1 is a front perspective view of a suture hook handle and suture hook constructed in accordance with the principles of this invention.

The suture hook system 10 as shown in the drawings comprises handle 12 and suture hook 14. It will be understood that suture hook 14 may be provided in a variety of lengths, diameters and needle curves. Handle 12 is provided near its distal end with a pair of rotatable wheels 16 and 18 which are mounted with their axes 20 and 22 parallel to each other and spaced apart symmetrically about the handle axis 24. The wheels each have a perimeter which may be covered with a polymeric or otherwise friction enhancing surface 26. The surface 26 may be ribbed or smooth, or may have a central smooth band portion bounded by ribbed band portions. The wheels are mounted in such a way that their perimetral surfaces contact each other at the nip 28 of the wheels. In the preferred embodiment nip 28 lies on axis 24. As will be understood below, rotation of either one of the wheels 16, 18 will cause rotation of the other wheel and will cause suture 27 (situated between the wheels) to be urged along suture path 29.

Handle 12 is provided near its distal end 15 with a collar 30 which is adapted to rotate within a limited range about axis 24 in order to lock suture hook 14 to handle 12 as will be understood below.

Collar 30 has a transverse distal end wall 32 in the form of a radially inwardly extending flange defining a circular aperture 34 concentrically aligned about axis 24. Aperture 34 is further provided with a pair of diametrically opposed keyways 36, 38. As will be explained below, keyways 36 and 38 facilitate the engagement of suture hook 14 with handle 12.

Figure 5:
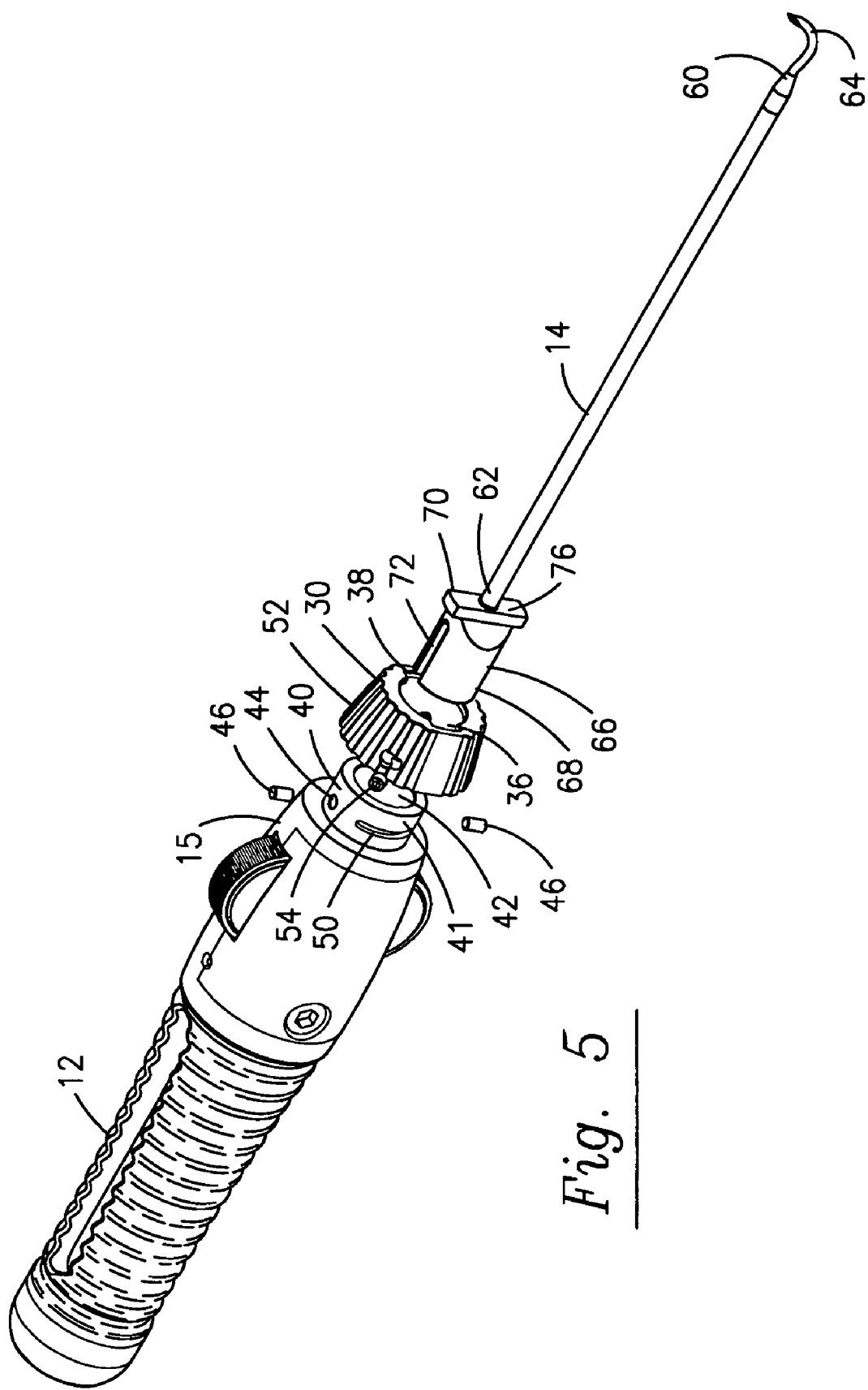
FIG. 5 is a front perspective exploded view showing the various parts of the invention in relation to each other.
Figure 9A:
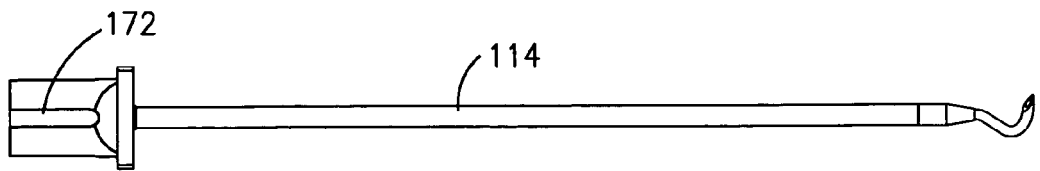
FIG. 9*a* is a side elevational view of a suture hook for use with the suture hook handle shown in FIG. 1.
Figure 9B:
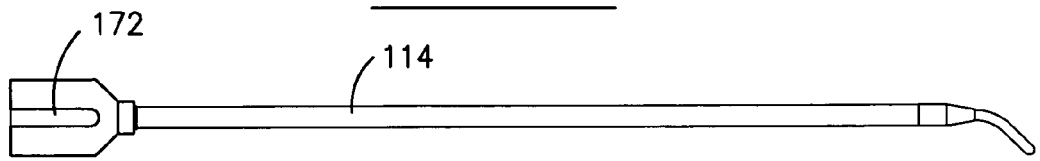
FIG. 9*b* is a top plan view of FIG. 9*a*.
Figure 9C:
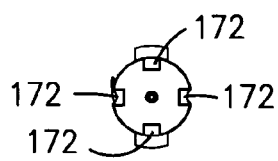
FIG. 9*c* is a left end view of FIG. 9*a*.
Figure 9D:
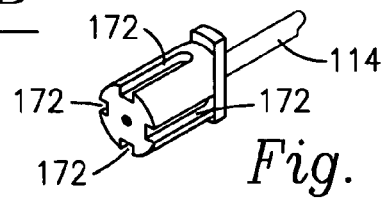
FIG. 9*d* is a left side perspective view of FIG. 9*a*.
Figure 10A:
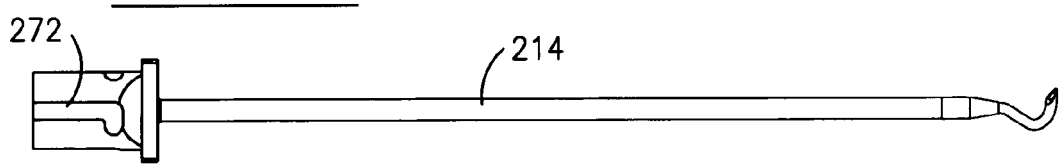
FIG. 10*a* is a side elevational view of a suture hook for use with the suture hook handle shown in FIG. 1.
Figure 10B:
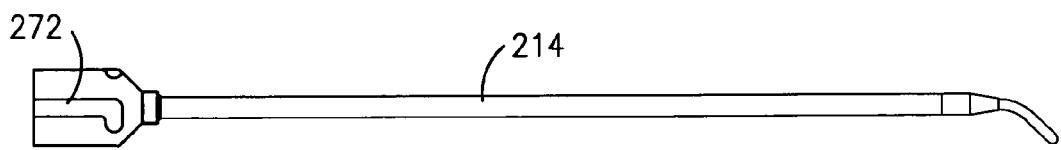
FIG. 10*b* is a top plan view of FIG. 10*a*.
Figure 10C:
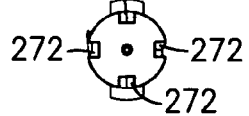
FIG. 10*c* is a left end view of FIG. 10*a*.
Figure 10D:
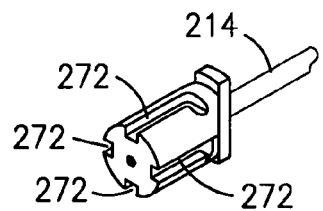
FIG. 10*d* is a left side perspective view of FIG. 10*a*.

As will be noted in FIG. 5, collar 30 is situated over a distal extension member 40 situated at the distal end 15 of handle 12. Extension 40 has a cylindrical external surface 41 and defines a recess 42 for receiving a proximal portion of the suture hook 14 as will be explained below. Extension 40 further comprises a pair of diametrically opposed throughbores 44 (only one of which is shown in FIG. 5), each throughbore adapted to receive a guide pin 46 which extends through the wall of the extension 40 and partially into recess 42 (as best seen in FIG. 7). Extension 40 is also provided on its exterior surface with a diametrically opposed pair of cam tracks 50 (only one of which is shown in FIG. 5) which are slightly helically situated about axis 24. When collar 30 is assembled with handle 12, its peripheral wall 52 will cover extension 40 and collar 30 will be rotatably attached to the handle via diametrically opposed pins 54 (only one of which is shown in FIG. 5) which extend through wall 52 and into cam track 50. It will be understood that the two ends of cam tracks 50 serve to limit the rotation of collar 30 about axis 24 by virtue of the abutment of pins 54 against the ends of the cam tracks 50.

Suture hook 14 has a distal end 60 and a proximal end 62. Distal end 60 is provided with a conventional hollow needle 64 having a predetermined shape. It will be understood that the suture hook system may be produced with suture hooks having a variety of distal tip shapes. Proximal end 62 of suture hook 14 is provided with a hub 66 comprising a body 68 of a given diameter and a transverse locking bar 70 of a greater diameter. The suture hook 14 may comprise a pair of concentric tubes as shown in FIG. 7, the outer tube serving as reinforcement for the inner tube which defines the actual lumen and needle tip. Body 68 is provided with a pair of diametrically opposed and longitudinally extending channels 72 (best seen in FIGS. 8c and 8d). Transverse bar 70 is fixedly secured to the distal-most end of body 68 and facilitates the engagement of suture hook 14 to handle 12.

Figure 4:
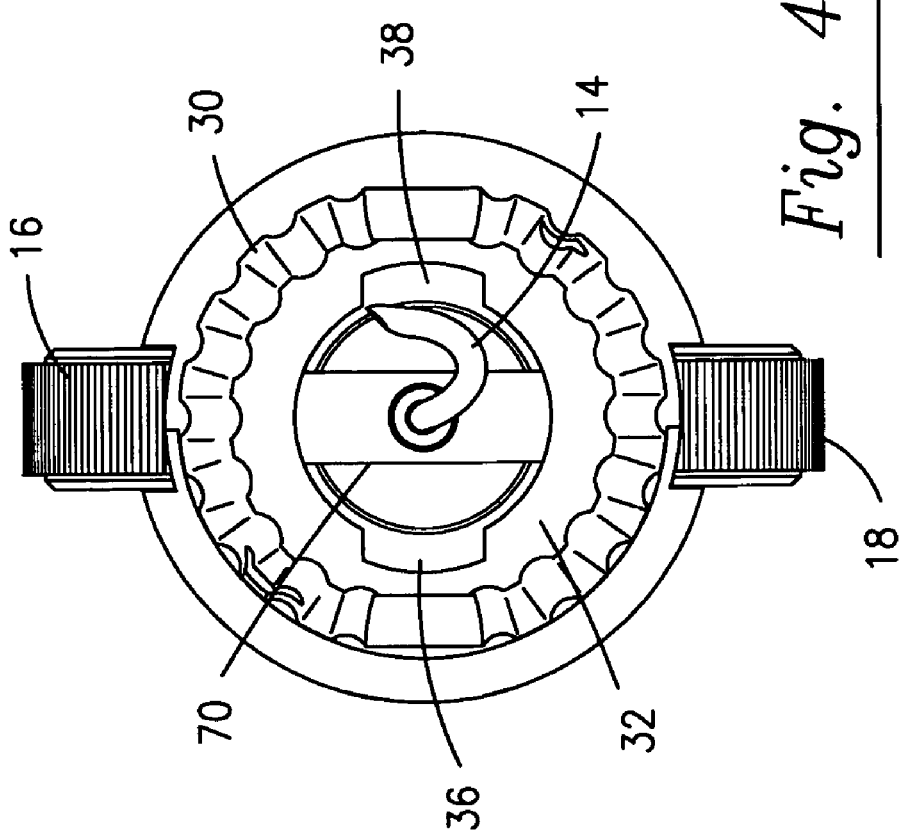
FIG. 4 is a view of FIG. 3 showing the suture hook handle in a locked position.
Figure 3:
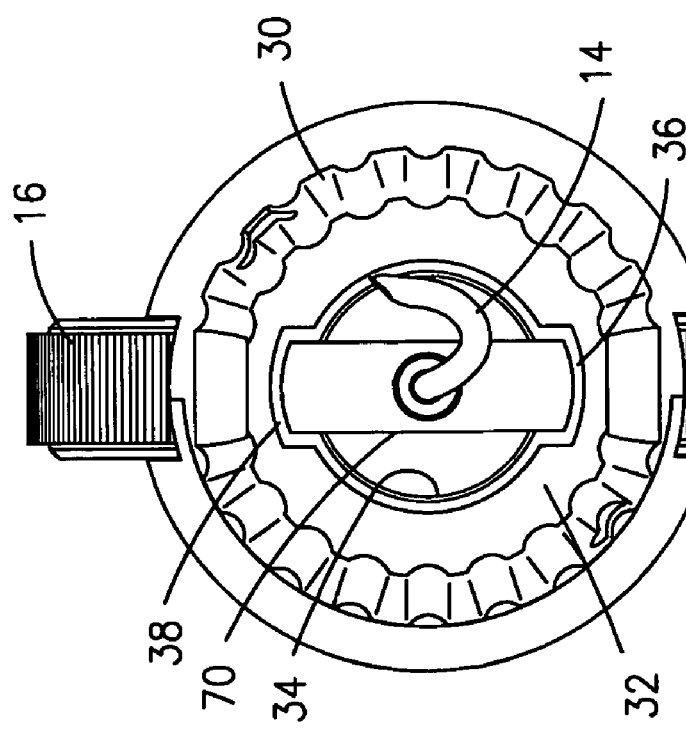
FIG. 3 is a right side elevational view of FIG. 1 showing the suture hook handle in an open position.

The method of attachment of suture hook 14 to handle 12 is best understood by reference to FIGS. 3 and 4. Prior to assembly of suture hook 14 with handle 12, the collar 30 is placed in an open or unlocked position as shown in FIG. 3. This enables aperture 34 to receive body 68 and further enables keyways 36 and 38 to receive transverse bar 70. As body 68 is moved further proximally into recess 42, the distal most surface 76 of transverse bar 70 will be situated proximal to the proximal side of flange 32 of collar 30. To accomplish this of course suture hook 14 must be rotated about axis 24 to align transverse locking bar 70 with keyways 36 and 38 while also aligning longitudinal grooves 72 with guide pins 46. When suture hook 14 is properly seated, collar 30 may be rotated from its open position shown in FIG. 3 to its locked position shown in FIG. 4, thereby retaining transverse bar 70 behind flange 32 and securing suture hook 14 to handle 12. As collar 30 is rotated from the open to the locked position, locking pins 54 slide within their respective grooves 50 to urge collar 30 slightly proximally to enhance the force with which flange 32 presses against the opposing ends of transverse bar 70. The degree of force thus exerted by collar 30 on transverse bar 70 may be varied by changing the pitch of the helical tracks 50. It will be further understood that the ends of the tracks near the locked position of collar 30 may be transverse rather than helical or may be provided with some other shape in order to securely lock collar 30 in place.

It will be understood that suture hook 14 may be easily repositioned to a different rotational position during a surgical procedure by momentarily disengaging it from handle 12, rotating it 180° about axis 24 and reattaching it.

Figure 2:
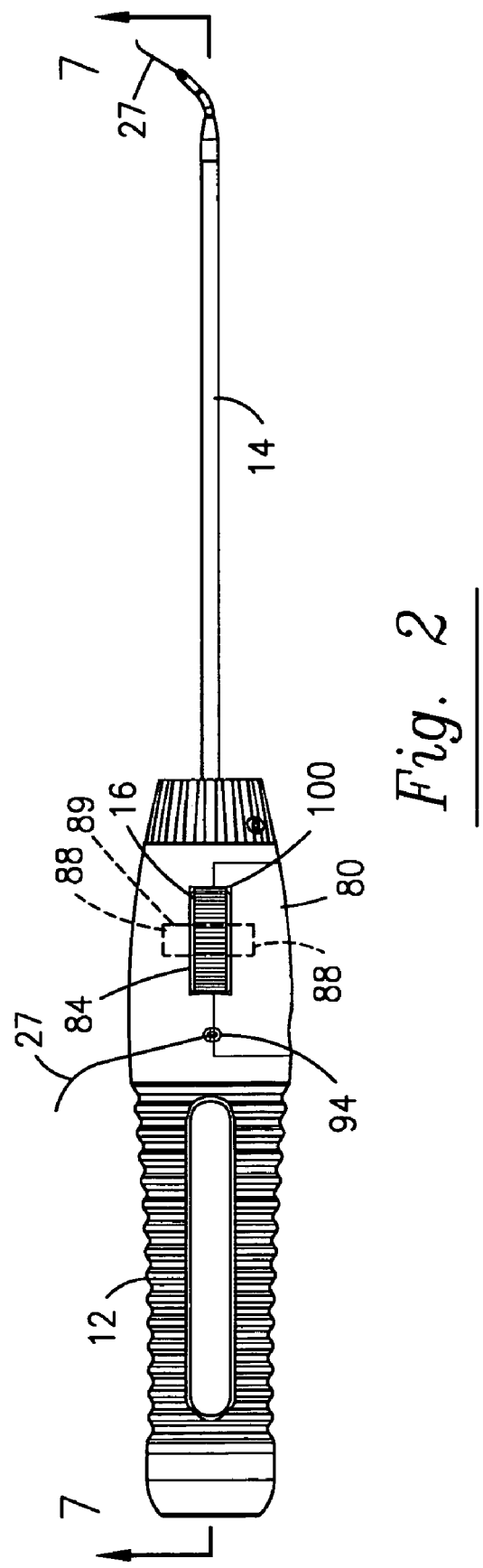
FIG. 2 is a top plan view of FIG. 1.

Referring now to FIGS. 1, 2 and 6 it is noted that handle 12 is provided with a removable cover 80 which comprises a portion of the outer surface of handle 12. The purpose of cover 80 is to enable handle 12 to have an ergonomically favorable external shape while also enabling handle 12 to be structured internally in such a way as to facilitate cleaning and repair of handle 12.

As best seen in FIG. 6, handle 12 is provided with a sagittal planar surface 82 aligned along axis 24 and extending transversely across the body of handle 12. In the preferred embodiment, handle 12 is further provided with a pair of recesses 84 and 86 which are adapted to receive wheels 16 and 18, respectively. (Alternatively, one recess could be adapted to retain both wheels.) Each wheel has an axis pin 88 which extends a predetermined distance transversely along the axis 20 of each wheel. Accordingly, recesses 84 and 86 are each provided with a central bore 89 for receiving axis pins 88 of each wheel. As best seen in FIG. 2, the bores 89 for receiving axis pins 88 extend into the body of handle 12 and into the cover 80. It will be understood that the depths of recesses 84 and 86 are preferably such as to receive one half the thickness of wheels 16 and 18. Symmetrical recesses are formed in cover 80 in order to enable wheels 16 and 18 to be aligned with axis 24 as best seen in FIGS. 2, 3 and 4.

Sagittal planar surface 82 is also provided with a pair of suture guiding channels 90 and 92 which extend between diametrically opposed openings 94 and 96 on the surface of handle 12 and a point adjacent and proximal to the nip 28 of the wheels 16 and 18. While a pair of suture guiding channels is provided in the preferred embodiment, this is to enable both right and left handed use of the device. Alternatively, only one channel may be provided. Sagittal planar surface 82 may also be provided with a channel 98 extending between a point adjacent to and distal to the nip 28 of the wheels and the proximal side of recess 42. It will be noted that the inside surface of cover 80, that is the surface which lies against saggital planar surface 82 when cover 80 is assembled with handle 12, need only be provided with recesses to receive axis pins 88. In the preferred embodiment, however, the cover is also provided with recesses 100 adapted to receive those sides of the wheels which are not received within recesses 84 and 86. That is, inside surface of cover 12 need not be provided with any grooves for guiding suture. It will be sufficient if grooves 90 and 92 are sufficiently large to accept the desired size suture. Alternatively, of course, passageways 90 and 92 may be formed by symmetrical and cooperating semi-circular grooves formed in sagittal planar surface 82 and the inside surface of cover 80. Additionally, while openings 94 and 96 are shown to be on the side of the handle, it will be understood that a single opening could be provided at the back of the handle so that the channel leading the suture to the nip of the rollers could be coaxial. The path followed by the suture is sometimes referred to herein as suture path 29.

The suture hook 14 shown in FIGS. 1 through 7 is shown in greater detail in FIGS. 8a through 8d. As noted, body 68 of suture hook 14 comprises a pair of diametrically opposed grooves 72. An alternative embodiment of a suture hook is shown in FIGS. 9a through 9d as suture hook 114 which comprises four straight and equiangularly spaced longitudinal grooves 172, thus enabling four discrete orientations of suture hook 114 about axis 24. Further embodiment of a suture hook is shown in FIGS. 10a through 10d as suture hook 214 having four equiangularly spaced longitudinal grooves 272, each of which is provided with a J-hook at its distal-most end to enable the suture hook to be locked to a suture hook handle without the need for a collar such as collar 30.

The proximal hubs of each of the suture hook embodiments are shown with a cylindrical configuration, the axis of body 68 being aligned with axis 24. It will be understood that body 68 may be made rectilinear so that its cross-section (transverse to axis 24) could be polygonal.

While collar 30 and its operation with locking tab 70 have been shown as a rotary embodiment, it will be understood that the invention could be redesigned as a linear embodiment in which the opening and closing of a locking mechanism could be effected by moving a collar longitudinally along the handle axis. For example, a quick lock mechanism could be used with a collar cam arrangement moving a plurality of circumferentially spaced fingers into and out of engagement with a groove on the hub of the needle.

Wheels 16 and 18 have been described as having their perimetral surfaces in contact with each other. It will be understood that the degree of contact is dependent upon the softness of the perimeter surface and the size of suture to be advanced. In some instances, contact may be unnecessary if the suture is large enough and the surface is able to "grip" the suture enough to advance it as one or both wheels roll. Thus, it is sufficient for the wheel perimeters to be adjacent to each other, it being understood that the term "adjacent" may require contact so the suture may be squeezed sufficiently to be advanced.

It will be understood that numerous other modifications and improvements may be made to the preferred embodiment of the invention disclosed herein without departing from the spirit and scope thereof.

What is claimed is:

1. In a suture passer comprising:
a handle having an axis, a proximal end and a distal end;
a path within said handle for guiding a suture to a predetermined point;
a hollow needle having a lumen, a proximal end and a distal end, and attachable to said handle at the distal end of said handle;
user-operable wheel means on said handle for engaging said suture at said predetermined point and moving it into the lumen of said hollow needle;
the improvement comprising:
connector means interposed between said distal end of said handle and said proximal end of said needle for attaching said needle to said handle in a selected one of a plurality of discrete predetermined rotational positions and holding said needle in the selected position;
wherein said connector means comprises:
an axially-extending projection formed on the distal end of said handle, said projection having a recess formed therein, said recess receiving a hub of said needle, said recess and said hub comprising cooperating longitudinal slots in one of said hub and said recess and transverse pins in the other of said hub and said recess, said slots and said pins being spaced radially around said hub and said recess, such that as said hub is inserted into said recess the hub and recess must be radially aligned such that said pins slide in said slots, such that said hub can only be received in said recess at a plurality of discrete radial positions,
a rotatable collar fitting over said projection and being formed to define a central aperture for receiving said hub of said needle, said collar having a flange extending inwardly from said aperture and having outwardly-extending keyways formed therein for receiving transversely-outwardly extending tabs formed on said hub, whereby said collar must be rotated to a specified position with respect to said projection in order that said cooperating longitudinal slots and transverse pins will allow said hub to be passed through the aperture in said collar and inserted into the recess formed in the projection, and whereby said collar can thereafter be rotated to a second position in order that said flange of said collar passes distally over the transversely-extending tabs on said hub, so as to retain said hub in a position fixed with respect to said body; and
means for securing said collar in said second position.

2. The suture passer of claim 1, wherein said means for securing said collar in said second position comprises at least one transverse pin retained in said collar that fits into a helical groove formed in the outer surface of said projection, whereby as said collar is rotated from said specified position to said second position said collar is urged proximally with respect to said handle, thereby being secured in place with respect to said handle.

3. The suture passer of claim 1, wherein said cooperating longitudinal slots and transverse pins formed on said recess and said hub comprise at least two longitudinally-extending slots on the hub and at least two pins retained by said projection and extending into said slots formed in said hub.

* * * * *